United States Patent [19]

Zoche

[11] Patent Number: 4,766,231

[45] Date of Patent: Aug. 23, 1988

[54] PROCESS FOR THE PREPARATION OF KETOXIMOSILANES

[75] Inventor: Günter Zoche, Bonn, Fed. Rep. of Germany

[73] Assignee: Dynamit Nobel AG, Troisdorf, Fed. Rep. of Germany

[21] Appl. No.: 128,879

[22] Filed: Dec. 4, 1987

[30] Foreign Application Priority Data

Dec. 6, 1986 [DE] Fed. Rep. of Germany ....... 3641756

[51] Int. Cl.$^4$ .............................. C07F 7/10; C07F 7/18
[52] U.S. Cl. ........................................................ 556/422
[58] Field of Search ......................................... 556/422

[56] References Cited

U.S. PATENT DOCUMENTS

| | | | |
|---|---|---|---|
| 4,705,877 | 11/1987 | Gornowicz et al. | 556/422 |
| 4,705,878 | 11/1987 | Gornowicz et al. | 556/422 |

FOREIGN PATENT DOCUMENTS

| | | | |
|---|---|---|---|
| 0082324 | 6/1983 | European Pat. Off. | 556/422 UX |
| 49-39967 | 10/1974 | Japan | 556/422 |
| 975603 | 11/1964 | United Kingdom | 556/422 UX |

OTHER PUBLICATIONS

Abstracts of SU-435-243 and SU-724-514 Chemical Abstracts CA:91718b and CA:93:132615j.

*Primary Examiner*—Paul F. Shaver
*Attorney, Agent, or Firm*—Felfe & Lynch

[57] ABSTRACT

Disclosed is a process for the production of ketoximosilanes and ketoximoalkoxysilanes. Ketoximes are reacted with alkyl trialkoxysilanes in the presence of a catalyst. The reaction is catalyzed by basic compounds which are dissolved or suspended in the ketoxime. The basic compounds that are used are alkali metals and, preferably, the oxides, hydroxides and carbonates of the elements from the 1st and 2nd group and the 3rd sub-group of the Periodic Table of Elements and lanthanides. The process according to the invention prevents the decomposition and explosion that easily occur in the known processes. The ketoximosilanes prepared according to the invention are valuable crosslinking agents for organopolysiloxane compositions.

6 Claims, No Drawings

PROCESS FOR THE PREPARATION OF KETOXIMOSILANES

BACKGROUND OF THE INVENTION

The subject matter of the present invention is a process for the preparation of ketoximosilanes and ketoximoalkoxysilanes. These silicon compounds are suitable especially as crosslinking silicon compounds in the production of compositions which can be hardened by exposure to moisture at room temperature to form elastomers, and which can be stored with the exclusion of water. Such compositions are obtained by mixing crosslinking compounds and diorganopolysiloxanes having condensable terminal groups.

It is known to prepare ketoximosilanes by the reaction of alkyl trichlorosilanes with ketoximes (cf. DE-PS No. 13 01 140, EP-A2-0 082 324, SU Pat. Nos. 435,243 and 724,514). In the performance of this process there is always the danger that ketoxime or ketoximosilanes will come in contact with substances of an acid nature. The intermediate formation of HCl will then form the hydrochloride of the ketoxime. For example, methylethylketoxime boils at standard pressure at 152° C., while its chloride decomposes very violently at a temperature as low as 50° to 70° C. Such decompositions can also be triggered by catalytic amounts of, e.g., ferric chloride. Ketoximosilanes under such conditions have a tendency to decompose explovively. L. J. Tyler (Chem. Eng. News 52 (1974) 35, 3) reports on two violent explosions of this kind.

The problem therefore existed of finding a process for the preparation of ketoximosilanes in which the danger of decomposition or explosion does not exist.

SUMMARY OF THE INVENTION

As a solution of this problem, a process has now been found for the preparation of monoalkyl ketoximosilanes and/or monoalkyl ketoximoalkoxysilanes of the general formula $$R^1Si(ON=X)_{(3-a)}(OR^2)_a,$$

wherein a can assume values of 0 to 2, $R^1$ and $R^2$ identical or different alkyl moieties with 1 to 6 carbon atoms, and X is a group of the formula $CR^1R^2$. The monoalkyl ketoximosilanes and/or ketoximoalkoxysilanes are formed by reacting an alkyl trialkoxysilane of the formula $R^1Si(OR^2)_3$ with a ketoxime of the formula $HON=X$ in the presence of alkali metals or of at least one basic compound of elements from the 1st or 2nd main group and 3rd subgroup of the Periodic Table of Elements and lanthanides.

In the fomulae, $R^1$ and $R^2$ can represent identical or different alkyl moieties, such as methyl, ethyl and iso-propyl moieties.

The reaction is catalyzed by the addition of basic substances. The catalysts are used in amounts of 10 to 200 mg per mole of alkoxysilane. The following are such catalysts: alkali metals dissolved in ketoxime, alkali metal carbonates and alkali metal hydroxides, and oxides and carbonates of the elements of the 2nd main group and 3rd sub-group of the Periodic Table of Elements and lanthanides. The preferred catalysts are the oxides and/or hydroxides of the alkaline earth metals.

In the reaction according to the invention, alcohol of the formula $R^2OH$ is released. This released alcohol is removed from the equilibrium by distillation through a column. Therefore, the combination of the starting products must be selected so that $R^2OH$ is the lowest-boiling component of all the reactants. The average number of alkoxy groups exchanged can be controlled by the following measures, used individually or in combination, which are known in themselves to the person skilled in the art:

1. Quantity ratio of alkoxysilane to ketoxime;
2. Reaction temperature level;
3. Duration of the reaction; and
4. Complete or incomplete removal of the released alcohol by distillation.

The reaction is generally performed at standard pressure. The reaction temperature can vary between 100° and 190° C. Ketoximosilanes containing predominantly alkoxy groups are formed at lower temperatures. Higher temperatures promote the complete separation of the alkoxy groups to the extent that corresponding stoichiometric amounts of etoximes are used.

The process according to the invention can be performed very simply. The starting materials are easily obtainable and commercially available. Further, during the process of the invention, acid does not form and hence there is no threat of an explosive state.

Where necessary, the process of the invention can be performed in a suitable solvent. However, it is another advantage of the process of the invention is that it can be performed without using a solvent, so that solvent circuits are not necessarily required in its technical practice.

EXAMPLE 1

Methyl-tris-(ethyl-methyl-ketoximo)-silane

The distillation apparatus consists of a 4-liter boiler flask with superimposed packed column (length: 83 cm; packging: Wilson glass spirals), an automatic column top, and a receiver flask.

The boiler flask is filled with 2198 g of methylethyl ketoxime (25.2 moles), 384 mg of calcium oxide, and 486 g of methyltrimethoxysilane (3.6 moles). Two hours of refluxing follow. Then methanol is distilled out at standard pressure in the course of 13 hours. The removal of methanol is ended when the top temperature has risen to about 135° C. The excess ketoxime is distilled out in vacuo and can be reused.

The raw product left in the boiler flask is distilled in a separate apparatus without a column, at 0.4 mbar and 99° to 101° C. 904 g of methyl-tris-(ethyl-methylketoximo)-silane is obtained.

EXAMPLE 2

$CH_3Si[ON=C(CH_3)((C_2H_5)]_{1.9}(OCH_3)_{1.1}$

Apparatus, input substances and amounts are identical to Example 1. In the procedure, however, the excess methanol distillation is stopped after 5 hours. In the methyl-ethyl-ketoxime then distilled off at about 1 mbar, no methanol can be detected by gas chromatography. By distillation at 0.4 to 0.5 mbar and 71° to 103° C., 763 mg of end product is obtained. By determination of the ketoximo groups it can be proven that this product contains an average of 1.9 ketoximo groups per mole.

EXAMPLES 3 to 8

The examples listed in the following table were aimed at achieving the most complete possible alkoxy group exchange at the highest possible yield. The performance of the examples is similar to that of Example 1.

Example 3 serves for purposes of comparison.

TABLE

| | INGREDIENTS | | | |
|---|---|---|---|---|
| EXAMPLE NO. | KETOXIME (moles) | SILANE (moles) | CATALYST (mg) | KETOXIMOSILANE PRODUCT (moles) |
| 3 | $HON=C(CH_3)(C_2H_5)$ (12.6) | $CH_3Si(OCH_3)_3$ (1.8) | none | $CH_3Si[ON=C(CH_3)(C_2H_5)]_3$ (0.6) |
| 4 | $HON=C(CH_3)(C_2H_5)$ (12.6) | $CH_3Si(OCH_3)_3$ (1.8) | Na (103) | $CH_3Si[ON=CH(CH_3)(C_2H_5)]_3$ (1.3) |
| 5 | $HON=C(CH_3)(C_2H_5)$ (5.4) | $(CH_3-CH_2-CH_2)Si(OCH_3)_3$ (0.6) | $La_2O_3$ (93) | $(CH_3-CH_2-CH_2)Si[ON=C(CH_3)(C_2H_5)]_3$ (0.4) |
| 6 | $HON=C(CH_3)(C_2H_5)$ (5.4) | $[(CH_3)_2CH-CH_2]Si(OCH_3)_3$ (0.6) | $Sm_2O_3$ (97) | $[(CH_3)_2CH-CH_2]Si[ON=C(CH_3)(C_2H_5)]_3$ (0.4) |
| 7 | $HON=C(CH_3)(C_2H_5)$ (5.4) | $CH_3Si(OC_2H_5)_3$ (0.6) | $CaCO_3$ (95) | $CH_3Si[ON=C(CH_3)(C_2H_5)]_3$ (0.3) |
| 8 | $HON=C(CH_3)_2$ (10.8) | $CH_3Si(OCH_3)_3$ (1.8) | $Mg(OH)_2$ (197) | $CH_3Si[ON=C(CH_3)_2]_3$ (1.2) |

It will be understood that this specification and examples are illustrative but not limitative of the present invention and that other embodiments within the spirit and scope of the invention will suggest themselves to those skilled in the art.

What is claimed is:

1. A process for the production of a ketoximosilane of the formula

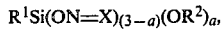

$R^1Si(ON=X)_{(3-a)}(OR^2)_a$, in which a can assume values from 0 to 2, $R^1$ and $R^2$ represent identical or different alkyl moieties with 1 to 6 carbon atoms and X is a group of the formula $CR^1R^2$, comprising: reacting a ketoxime of the formula $HON=X$ with an alkyl trialkoxysilane of the formula $R^1Si(OR^2)_3$ in the presence of an alkali metal or of at least one basic compound of an element selected from the 1st and 2nd main group and the 3rd secondary group of the Periodic Table of Elements and lanthanides.

2. The process of claim 1, wherein the alkali metal or basic compound is in its hydroxide, oxide or carbonate form.

3. The process of claim 1, wherein the alkali metal or basic compound is used in an amount of 10 to 200 mg per mol of input alkyl trialkoxysilane.

4. The process of claim 1, wherein the reaction is performed in a solvent-free manner.

5. The process of claim 1, wherein the alkali metal compound is used in an amount of 10 to 200 mg per mol of input alkyl trialkoxysilane.

6. The process of claim 2, wherein the reaction is performed in a solvent free manner.

* * * * *